United States Patent [19]

Englert et al.

[11] Patent Number: 4,707,235
[45] Date of Patent: Nov. 17, 1987

[54] ELECTROPHORESIS METHOD AND APPARATUS HAVING CONTINUOUS DETECTION MEANS

[75] Inventors: David F. Englert, Plainfield; Richard J. Wheeler, Warren, both of N.J.

[73] Assignee: Pharmacia, Inc., Piscataway, N.J.

[21] Appl. No.: 787,904

[22] Filed: Oct. 16, 1985

[51] Int. Cl.$^4$ .............................................. C25B 7/00
[52] U.S. Cl. ............................... 204/182.8; 204/182.7; 204/299 R; 250/374
[58] Field of Search ............. 204/299 R, 182.8, 182.7; 250/374, 375

[56] References Cited

U.S. PATENT DOCUMENTS

| | | | |
|---|---|---|---|
| 2,502,683 | 4/1950 | Wannier | 250/374 X |
| 3,432,414 | 3/1969 | Rand | 204/182.8 |
| 3,969,218 | 7/1976 | Scott | 204/299 R |
| 4,019,057 | 4/1977 | Bram | 250/374 X |
| 4,035,377 | 7/1977 | Detroy | 204/182.8 X |
| 4,198,389 | 4/1980 | Wadsworth | 204/182.8 X |
| 4,207,166 | 6/1980 | Dahms | 204/182.8 X |
| 4,305,799 | 12/1981 | Schwarz et al. | 204/182.8 X |
| 4,311,908 | 1/1982 | Goulianos et al. | 250/374 |
| 4,456,513 | 6/1984 | Kawai et al. | 204/299 R X |
| 4,534,647 | 8/1985 | Gross et al. | 204/299 R X |

FOREIGN PATENT DOCUMENTS 59-193355 11/1984 Japan .

OTHER PUBLICATIONS

Lea, D. J., et al., *Laboratory Practice*, vol. 24, No. 8, pp. 523-524, (1975).

Primary Examiner—T. Tung
Attorney, Agent, or Firm—Donald E. Egan

[57] ABSTRACT

A multi-channel electrophoresis apparatus is fitted with a detection means disposed substantially across the width of the medium, intersecting all channels. The detection means senses components of samples as they migrate past the detection means and identifies the channel in which the detected components are located. In the preferred embodiment, the samples are tagged with radioisotopes which are detected by the detector.

25 Claims, 6 Drawing Figures

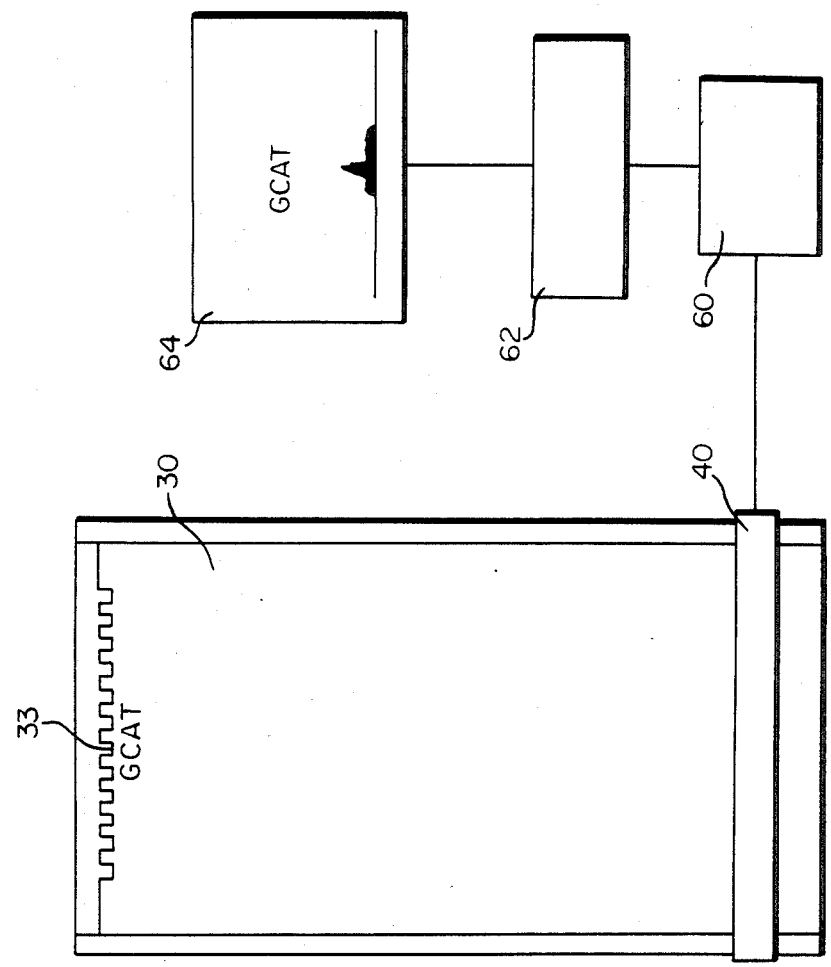
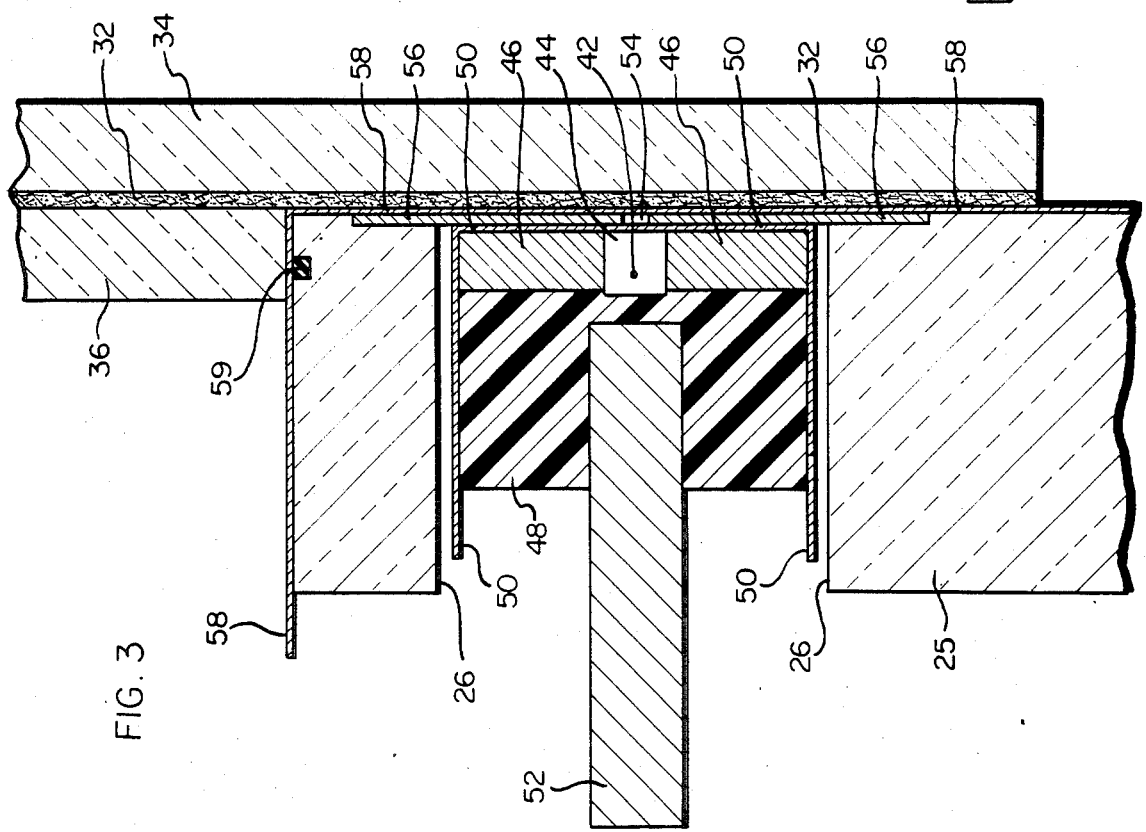

ELECTROPHORESIS METHOD AND APPARATUS HAVING CONTINUOUS DETECTION MEANS

The present invention relates to an analytical device for electrophoretically separating samples into a plurality of components and continuously detecting the separated components simultaneously for a plurality of samples. More particularly, the present invention relates to a continuous electrophoresis system adapted to run multiple samples simultaneously using online detectors to simultaneously convert the read-out from the detectors to electronic signals.

BACKGROUND OF INVENTION

It is a common practice in biological experimentation to separate molecules according to their relative mobilities through a polymer network under the influence of an electric potential. As commonly practiced, this technique of electrophoresis is done by applying several samples to one end of a thin slab of the polymer network or gel and applying an electric potential to the gel for a certain period of time, so that charged components of the samples move in parallel directions for various distances depending on their relative mobilities which depend on their chemical natures. After the period of electrophoresis, the location of the various components in the gel are determined by various means.

In some experiments, components of the samples are rendered radioactive and their locations are determined by detecting ionizations produced by the radioactive disintegrations. The most common means of identifying the position of the radioactive components in the gel is by the process of autoradiography, whereby a photographic emulsion is apposed to the gel for a period of time which may range from several hours to several days. Ionizing radioactivity causes silver grains in the emulsion to develop at positions correponding to the positions of the various radioactive components of the samples. The amount of radioactivity in the various components can be approximated by the optical density of the developed photographic emulsion.

This technique is used in procedures for the determination of the sequences of nucleotides in nucleic acid chains as described by Maxam et al., Proc. Natl. Acad. Sci., 74,560 (1977), by Sanger et al., Proc. Natl. Acad. Sci., 74,5463 (1977), and by Simoncsits et al., Nature 269,833 (1977). In these procedures, 4 or 5 samples containing nucleic acid chains labeled with phosphorus-32 migrate simultaneously in adjacent channels of a polyacrylamide electrophoresis gel for a predetermined period of time. The nucleotide sequence is determined by noting the relative positions on the autoradiograph of radioactively labeled components in the 4 or 5 adjacent channels. The radioactive components are well separated only toward the anodic end of the electrophoresis gel, and the same samples are usually electrophoresed two or three times for different time periods, or on different electrophoresis gels, so that all the radioactive components of interest are well separated at the anodic end of a gel at least once to acquire all the required sequence information.

An alternative to autoradiography for determining the positions of ionizing radioactivity in electrophoresis gels is by detecting ionizations produced in a gas by the use of a position sensitive radiation detector. Such devices have been reported by Gabriel et al., FEBS Letters 39,307 (1974), Markham et al., Nuclear Inst. and Methods 160,49 (1974), Goulianos et al., Anal. Biochem. 103,64 (1980), and Petersen et al., Nuclear Inst. and Methods 176,239 (1980). A device which uses a position sensitive radiation detector for detecting the position of radioactivity in electrophoresis or chromatography supports was disclosed in U.S. Pat. No. 4,019,057 to Bram.

The resolution with which these position sensitive detectors localize the radioactively labeled material depends on several factors, including the energy of the ionizing particle. Resolution is generally poorer for highly penetrating particles, such as the beta particles from phorphorus-32 (0.70 MeV average energy). Markham et al., Nuclear Inst. and Methods, 160,49 (1979), reported resolution of 2.2 to 3.8 mm full width at half maximum (FWHM) for localizing phosphorus-32 with their device. For experiments such as nucleic acid sequencing, this degree of resolution would not be adequate to resolve components in the direction of electrophoretic migration because the radioactive components are not separated by greater than 2 mm except at the anodic end of the electrophoresis gel. The degree of resolution could be adequate to resolve components in different channels corresponding to the various samples.

In many laboratories, DNA sequencing, has become a routine, but somewhat tedious procedure. The protocol for carrying out DNA sequencing using electrophoresis is a manual-intensive (rather than instrument-intensive) procedure which requires attention over an extended period of time to complete the analysis of a single sequencing experiment. Even after the electrophoresis experiment, which may require 24 hours, has been run, the exposure of the x-ray film necessary to get a read-out may require an additional 16–48 hours. Thus, it is not uncommon to have a two day hiatus between the completion of the DNA synthesis or modification and the analytical results from the electrophoresis.

SUMMARY OF THE PRESENT INVENTION

The present invention provides an apparatus and a method of using such apparatus which is adapted to separate samples into a plurality of components and to continuously detect the position of the separated components simultaneously for a plurality of samples using an online detector which continously provides a read-out of the data in electronic form. The present invention thus provides the experimenter with virtually instantaneous read-out of data from the electrophoretic fractionation of the samples.

In its broadest embodiment, the present invenion contemplates an apparatus which carries out electrophoresis on a continuous basis, with multiple samples, using online detection to simultaneously detect components of multiple samples as those components pass by the detector and convert the data from the detector into electronic signals.

The present invention is not restricted to any specific electrophoresis media. Generally, acrylamide gels or agarose gels, such as those which are in current use, may be employed in the apparatus of the present invention. Gels containing from about 4% to 20% by weight of polymer in a trisborate buffer with 6 molar urea are generally preferred for nucleic acid sequencing, but the present invention may be applied to other types of gel structures.

In the preferred embodiment, the components of the samples are labeled radioactively using well known techniques and the detection system is a radiation detector, as is more fully described below. However, the present invention broadly contemplates the use of other radioisotope detectors, UV absorption detectors, fluorescence detectors, phosphorescence detectors, luminescence detectors and position sensitive chemical detectors.

A variety of radioisotope detection devices may be used, including scintillators coupled to photomultipliers, solid state detectors and microchannel plates. However, the radioisotope detector described below is preferred.

The present invention provides for immediate readout of preliminary data from electrophoresis analysis. The preliminary data is advantageous in that it can be used to modify the conditions of the electrophoresis (e.g., temperature or voltage) during the separation and thus control the rate of migration of the fractions through the gel. It also may be used to match the migration rate, using voltage control, to the detector capability. Still further, the present invention permits the user to immediately abandon an unsuccessful test.

The apparatus of the present invention may be used to analyze anything which can be separated by an electric field. Using the radiation isotope detector of the preferred embodiment, this apparatus may be used to analyze any products labled with P-32 phosphorus or other emitters of penetrating beta particles.

The present invention broadly contemplates the convenient characterization of polymers, and specifically contemplates the separation of particles of DNA molecules, polypeptide molecules, protein molecules, nucleic acid molecule, carbohydrate molecules, chromosomes, from a variety of sources, including procaryotes, yeast, plants, animals, and humans.

Additional advantages of the present invention include:

The device of the present invention can be run with a single loading of samples for DNA sequencing which will not require constant attention or further loadings. Thus, there will be a cost reduction in terms of labor savings, and more information could be obtained per gel.

Because smaller size gels may be used, gels will be easier to make. It will not be necessary to pour gradient gels. The present invention contemplates the use of stock or pre-made gels. Gels may be used more than once, thus minimizing the time spent in preparing gels.

About 24 samples may be loaded across a 25 centimeter gel, making possible the collection of sequence data from up to 6 DNA segments of up to 400 or more nucleotides in each overnight run.

After the samples are loaded, the gel will not have to be handled except for disposal. Thus, the tedious and time consuming steps of gel fixing, drying and autoradiography are eliminated. Current autoradiographic techniques sometimes use two films per gel in order to account for the difference in intensity between the top and the bottom of the gel. In the present invention, film will not have to be used and darkroom time will not have to be scheduled.

Gel drying facilities, film cassettes, x-ray film, $-70°$ C. freezer space, photographic chemicals and trays and darkroom will not be required. X-ray film costs up to $3.00 per sheet. If 200 sequencing gels are run per year, over $3,000.00 is spent on film in 5 years. Space in low temperature freezers is usually valuable.

Manual reading of the film will not be necessary, and computer interpretation of the data will be possible without investment in a scanner or video camera image analysis system. The bands will be spaced approximately uniformly in the temporal record, facilitating machine interpretation using only computer software.

Finally, there will be no moving parts in the instrument making it more reliable than many other instruments.

These and other advantages are provided by the present invention wherein radioactive components of samples are detected online as they migrate through the electrophoresis gel. Multiple samples, migrating through different channels, are continuously detected as ionization produced in a gas as the components migrate past a narrow window in front of the gas containment. A position sensing device is provided for localizing the inoizations from the radioactivity along the long dimension of the narrow window, in order to determine in which channels the radioactive components are located. The radioisotope detector is positioned near the anodic end of the electrophoresis gel so that various radioactive components are detected sequentially after they have been separated by migrating nearly the full length of the gel from the cathodic end and are, therefore, maximally separated from each other.

The apparatus of the present invention permits the use of shorter electrophoresis gels than those used conventionally for nucleotide sequencing experiments. Thus, the apparatus of the present invention permits the sequencing of long nucleotide sequences (300–400) with a single application of each of the 4 or 5 different samples to the electrophoresis gel. Thus, the apparatus of the present invention provides electronic data, on a continuous basis, for multiple samples in different channels on a continuous basis wherein the early data from the experiment is promptly available to the experimenter.

BRIEF DESCRIPTION OF THE DRAWINGS

The advantages of the present invention will become apparent from the following description when taken in conjunction with the accompanying drawings, of which:

FIG. 3 is a fragmentary diagram of an embodiment of the position sensitive radiosotope detector taken in cross section at 3—3 of FIG. 1, showing the interface with the electrophoresis gel;

FIG. 4 is a schematic diagram of the electrophoresis apparatus and the electronic system;

DETAILED DESCRIPTION OF THE PREFERRED EMBODIMENTS

Figure 1:
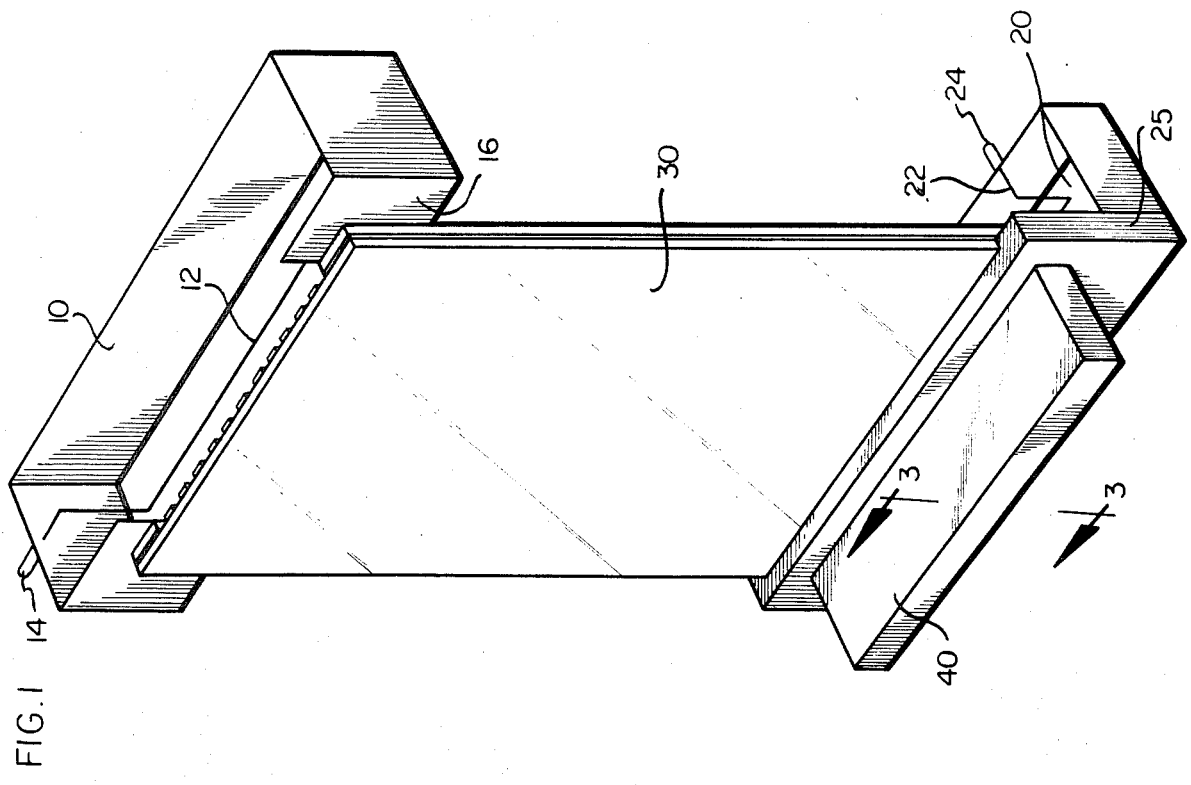
FIG. 1 is a perspective view of the electrophoresis apparatus and position sensitive radioisotope detector.

Referring to FIG. 1, the apparatus of the present invention generally comprises an upper buffer reservoir 10, a lower buffer reservoir 20 and gel assembly 30 which extends from the upper buffer reservoir 10 to the lower buffer reservoir 20. The detector 40 is positioned across the gel assembly 30 adjacent to lower buffer reservoir 20.

Figure 2:
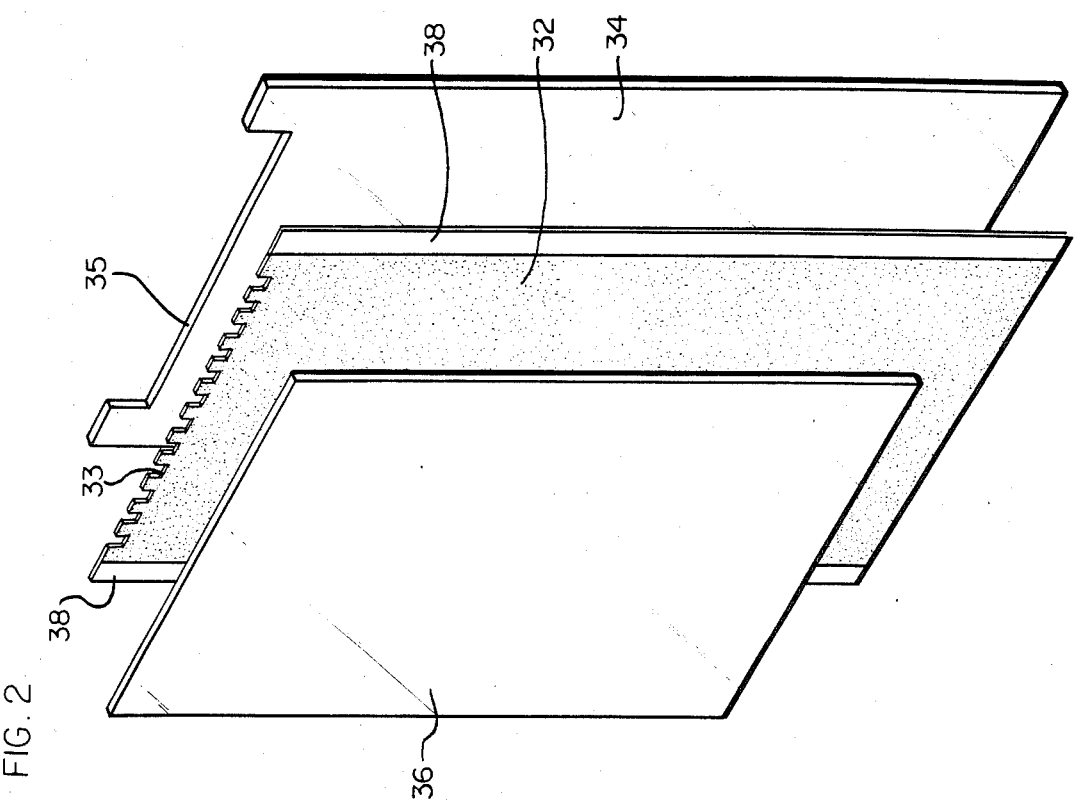
FIG. 2 is a fragmentary diagram if the electrophoresis apparatus showing the components of the electrophoresis gel assembly.

The electrophoresis gel assembly 30, shown more particularly in FIG. 2, incorporates a gel 32 which has typical dimensions of 300 mm high and 200 mm wide and 0.3 mm thick. The gel 32 is cast between the two glass plates 34 and 36 of approximate thickness 3 mm. Spacers 38 of approximate 0.3 mm thickness determine the thickness of the electrophoresis gel 32. The gel 32 is provided with multiple sample wells 33 along the top edge. Wells 33 are filled with electrophoresis buffer, and the samples are introduced into them. Glass plate 36 is about 250 mm high and 200 mm wide. Glass plate 34 has dimensions 300 mm high and 200 mm wide. The position sensitive radioisotope detector 40 is positioned at the lower end of the gel 32, separated from the sample wells 33, apposed to the electrophoresis gel 32 below glass plate 34. The electrophoresis gel medium in the region of detector 40 may be of a different nature than the medium in the upper 250 mm of the gel.

Upper buffer reservoir 10 contains an electrophoresis electrode 12 connected to terminal 14 for connection to the electrophoresis power supply (not shown). Upper buffer reservoir 10 comprises a notched wall 16 affixed to the gel assembly 30 and positioned to cooperate with notch 35 in glass plate 34 and thus communicate the buffer in upper reservoir 10 with the gel 32 of gel assembly 30.

Lower buffer reservoir 20 also includes a electrophoresis electrode 22 and terminal 24. Lower buffer reservoir 20 includes a supporting wall 25 having opening 26 adapted to receive detector 40. As can be more readily seen from FIG. 3, the gel assembly 30 is positioned adjacent to supporting wall 25 whereby the gel 32 is juxtaposed on detector 40.

FIG. 3 shows the preferred embodiment of the position sensitive radioisotope detector 40 and the details of the interface of the detector 40 with the electrophoresis gel 32.

The detector 40 comprises anode wire 42 positioned within gas chamber 44. A counting gas (90% argon, 10% methane) is contained within chamber 44. The sides of gas chamber 44 are defined by aluminum walls 46 (2 mm thick). The back of chamber 44 is defined by partition 48 which may be comprised of G10 phenolic material and which may be slightly indented to give a chamber 2.0 mm high and 2.1 mm wide. Aluminized polyester film 50 is wrapped around partition 48, and walls 46 and thus defines the front side of gas chamber 44. The aluminized polyester film 50 is 0.012 mm thick, and is positioned with the aluminized face away from anode wire 42. The anode wire 42 is 0.020 mm in diameter and made of gold-plated tungsten-rhenium. Anode wire 42 is positioned about 1.3 mm from the aluminum polyester film 50. Electromagnetic delay line 52 is positioned adjacent to gas chamber 44 within partition 48.

The aluminum walls 46 are maintained at ground potential. The aluminum coating on the aluminized polyester film 50 is also at ground potential. The windings of electromagnetic delay line 52 are connected to ground potential by 100K resistors.

The window 54 through which detector 50 reads radioactivity is defined by lead shields 56 which are 0.35 mm thick. The width of the window may vary, but a window of 0.5 mm provides good results.

Plastic film 58 of 0.025 mm thickness is wrapped around the upper end of supporting wall 25 and over lead shield 56, including window 54. Supporting wall 25 is provided with gasket 59 to seal wall 25 to the gel assembly 30 from the atmosphere.

In the operation, the radioactive components of the samples passing through the electrophoresis gel 32 are read as the components pass by window 54 in lead shield 56. The beta particles from phosphorus-32 have sufficient energy to produce inonizations which are detected by detector 40. Ionizing radiation of sufficient energy from radioactive components within the electrophoresis gel 32 passes through window 54 to produce ionizations in the gas in chamber 44 of the detector 40. Free electrons formed by ionizations in the counting gas in chamber 44 are accelerated to anode wire 42 which is connected to a voltage of about 1,250 volts.

The overall operation of the invention is illustrated in FIG. 4. Samples containing radioactive components are loaded into wells in the top or cathodic end of the electrophoresis gel assembly 30 and migrate in the electric field to the bottom of the gel. When the radioactive components pass in front of the window 54 in the lead shield 56 of detector 40, ionizations and electronic avalanches occur near the anode wire. These electronic signals are detected and localized by the electromagnetic delay line 52 and associated electronic circuitry 60, and this information is stored by the computer 62.

Data are accumulated for a period of time, typically 30 seconds, and displayed in a histogram 64 which gives the distribution of the radioactive components in the different channels. Such histograms are stored for successive time periods during an electrophoresis experiment to obtain simultaneous records for all the channels of the quantity of various radioactive components as a function of time which corresponds to their electrophoretic mobilities.

The following example will serve to illustrate the use of electrophoresis apparatus of the present invention and the results attained thereby, but it is understood that this example is set forth merely for illustration and many other compounds may be analyzed using the present invention using suitable variations therein.

EXAMPLE I

Figure 5:
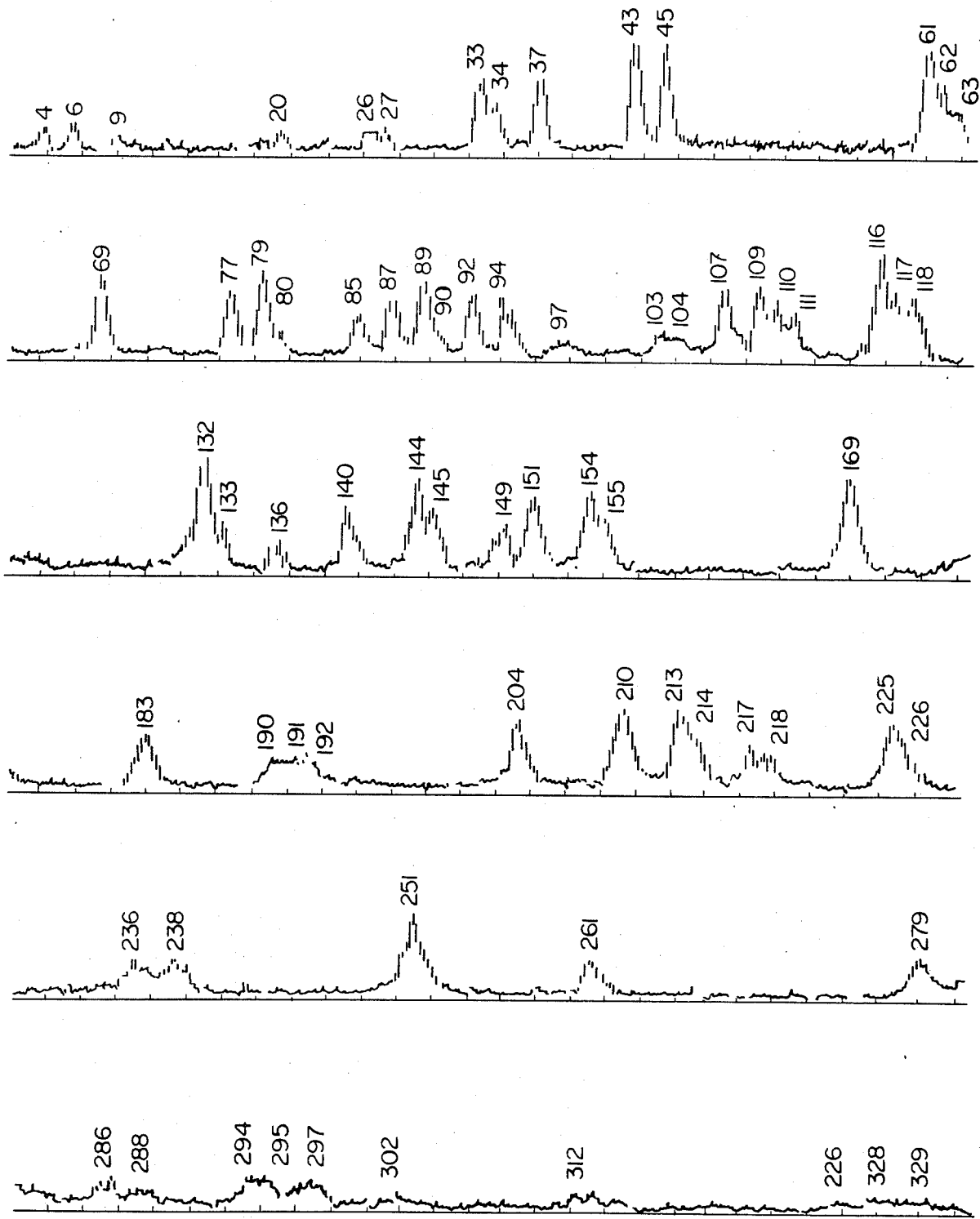
FIG. 5 is a graphical presentation of the temporal record of the radioactive components electrophoretically migrating past the detector window in one channel of an electrophoresis gel.

Results of a DNA sequencing experiment performed with the apparatus of the present invention are shown in FIG. 5. The radioactive components in the channel which gives the positions of thymidylic acid nucleotides in the DNA sequence are shown as a function of time. The numbers in the figure indicate the position of the thymidylic acid nucleotides counting from a restriction site in the DNA. The radioactive components are well separated and uniformly spaced past 200 nucleotides.

Figure 6:
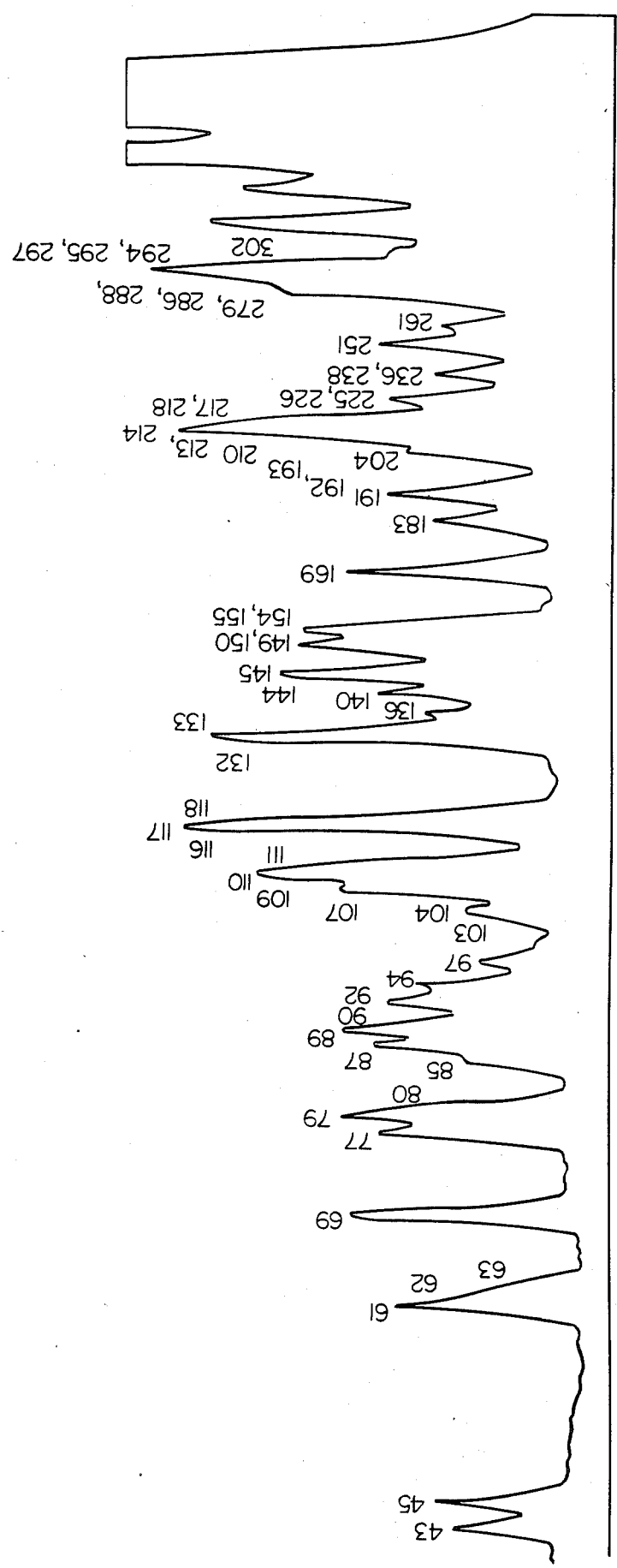
FIG. 6 is a densitometer scan of one channel of a film autoradiograph of an electrophoresis experiment performed according to the prior art.

A densitometer scan of the thymidylic acid channel of a film autoradiograph of a DNA sequencing gel is shown in FIG. 6. The numbers indicate the positions of the thymidylic acid nucleotides in the DNA sequence and correspond to the numbers in FIG. 5. The left side of the figure represents the bottom of the gel. The radioactive components corresponding to the first 41 nucleotides of the sequence have passed off the bottom of the gel. About 60 or 70 nucleotides of the sequence can be determined from the bottom part of the autoradiograph, but above that the components are too close together to be resolved. At least 2 or 3 loadings of the samples, electrophoresed for different periods of time, would have been necessary to determine 200 or more nucleotides of the sequence.

Thus, this invention provides an improvement of the prior art for determining the relative electrophoretic mobilities of radioactively labeled materials, especially for sequencing nucleic acid chains. Data are acquired and stored electronically. This makes unnecessary the exposure and processing of photographic film and the manual reading of the developed autoradiograph. The data can be processed and analyzed automatically by a computer. The 4 or 5 samples required for the sequencing of nucleic acid chains need be loaded only once to a relatively short electrophoresis gel.

Those skilled in the art will recognize that many modifications may be made to the specific embodiment just disclosed. For example, the position of electronic avalanches in the detector may be sensed by determining the division of charge between the two ends of a resistive anode wire. Also, a multistep avalanche detector such as that described by Petersen et al., Nuclear Inst. and Methods 176,239 (1980), may be used to localize ionizations within a gaseous medium. Also, the gas may be pressurized to enhance the detection efficiency and position resolution.

The scope of the invention herein shown and described are to be considered only as illustrative. It will be apparent to those skilled in the art that numerous modifications may be made therein without departure from the spirit of the invention and the scope of the appended claims.

We claim:

1. An apparatus for analytical electrophoresis comprising:
    a layer of electrophoresis medium having a plurality of channels, each of which is adapted to electrophoretically separate samples into components along said channels in the plane of said layer;
    means to introduce a plurality of samples having multiple components into one end of said medium in said plurality of channels;
    means to apply an electric potential to said medium along said channels;
    detection means disposed in a fixed position substantially across the width of said medium, intersecting said channels, said detection means being substantially separated from said sample introduction means, said detection means adapted to detect continuously in time during the electrophoretic migration said components of said samples in said channels and to identify the channel in which the detected components are located as said components pass through said medium adjacent to said detection means.

2. The apparatus as described in claim 1, wherein the components of said samples are labeled.

3. The apparatus as described in claim 2, wherein the components of said samples are radioactively labeled.

4. The apparatus as described in claim 3, wherein the detector comprises an integral position-sensitive radioisotope detector.

5. The apparatus as described in claim 4, wherein said detector comprises a narrow, elongated chamber for gas disposed within one millimeter of the electrophoresis medium, ionizable gas within said chamber, means to electronically amplify the ionizations produced in the gas by ionizing radiation, and means for electronically identifying the channel position of the amplified electrical discharges along the length of the contained gas.

6. The apparatus as described in claim 5, wherein ionizing radiation is admitted to the chamber through an elongated slit in a radiation absorbing material.

7. The apparatus as described in claim 6, wherein said slit is about 0.5–2.0 mm wide.

8. The apparatus of claim 7, wherein the radiation absorbing material is lead.

9. The apparatus of claim 1, wherein multiple detectors are disposed across said medium.

10. The apparatus of claim 1, wherein said medium is homogeneous in composition along said channels.

11. The apparatus of claim 1, wherein the medium has a composition gradient along the length of said channels.

12. A method of continuously analytically observing the separation of samples into a plurality of components by electrophoresis simultaneously for a plurality of samples which comprises:
    introducing samples containing multiple components into separate channels in an electrophoresis medium;
    subjecting said samples to an electric potential in said channels of said electrophoresis medium to cause components of each sample to migrate along said channel; and
    continuously in time detecting said components in each sample simultaneously during the electrophoretic migration, at a location separated from the position of sample introduction with a detector disposed in a fixed position substantially across the width of said medium, as said components pass through said medium in their respective channels.

13. The method as described in claim 12, wherein the components of said samples are labeled.

14. The method as described in claim 13, wherein the components of said samples are radioactively labeled.

15. The method as described in claim 14, wherein said components are labeled with phosphorus-32.

16. The method as described in claim 14 or 15, wherein passage of said labeled components of all samples are detected with a position-sensitive radioisotope detector disposed across said channels.

17. The method as described in claim 16, wherein the data collected by said detector is stored electronically.

18. The method as described in claim 17, wherein the data collected by said detector is accumulated for 30 seconds prior to storage.

19. The method as described in claim 18, wherein said collected data is displayed as a function of time.

20. The method as described in claim 12, wherein the electrical potential is maintained at the same level throughout the separation.

21. The method as described in claim 12, wherein the temperature of the electrophoresis medium is maintained at the same temperature throughout the separation.

22. Method of sequencing nucleic acids which comprises:
    introducing samples containing nucleotide chains into separate channels in an electrophoresis medium;
    subjecting said samples to an electric potential in said channels of said electrophoresis medium to cause nucleotide chains of each sample to migrate along said channel; and continuously in time detecting said nucleotide chains in each channel simultaneously during the electrophoretic migration, at a location separated from the position of sample introduction with a detector disposed in a fixed position substantially across the width of said medium, as said nucleotide chains pass through said medium in their respective channels.

23. The method as described in claim 22, wherein said nucleotide chains are labeled.

24. The method as described in claim 23, wherein said nucleotide chains are radioactively labeled.

25. The method as described in claim 24, wherein said nucleotide chains are labeled with phosphorus-32.

* * * * *